(12) United States Patent
Sahu et al.

(10) Patent No.: US 10,724,978 B2
(45) Date of Patent: Jul. 28, 2020

(54) SYSTEMS AND METHODS FOR ENVIRONMENT SENSING

(71) Applicant: Apple Inc., Cupertino, CA (US)

(72) Inventors: Saroj K. Sahu, Fremont, CA (US); Karthik Kadirvel, San Jose, CA (US)

(73) Assignee: Apple Inc., Cupertino, CA (US)

( * ) Notice: Subject to any disclaimer, the term of this patent is extended or adjusted under 35 U.S.C. 154(b) by 116 days.

(21) Appl. No.: 16/147,510

(22) Filed: Sep. 28, 2018

(65) Prior Publication Data

US 2019/0101501 A1    Apr. 4, 2019

Related U.S. Application Data

(60) Provisional application No. 62/566,295, filed on Sep. 29, 2017.

(51) Int. Cl.
*G01N 27/06* (2006.01)
*G06N 5/02* (2006.01)
*G01N 33/00* (2006.01)
*G01N 27/04* (2006.01)

(52) U.S. Cl.
CPC .......... *G01N 27/06* (2013.01); *G01N 27/045* (2013.01); *G01N 33/0031* (2013.01); *G01N 33/0073* (2013.01); *G06N 5/022* (2013.01)

(58) Field of Classification Search
CPC .. G01N 27/06; G01N 27/045; G01N 33/0031; G01N 33/0073
USPC ....................................................... 73/31.02
See application file for complete search history.

(56) References Cited

U.S. PATENT DOCUMENTS

2019/0234841 A1*  8/2019  Spencer ............... G01N 1/2273

* cited by examiner

*Primary Examiner* — Jamel E Williams
(74) *Attorney, Agent, or Firm* — Morgan, Lewis & Bockius LLP (57) ABSTRACT

A portable communication device includes one or more sensors, a pair of electrodes associated with each sensor, and a processing circuit configured to apply a bias supply voltage to the pair of electrodes and to process output signals from the sensors. Each sensor is an ionic liquid sensor tuned for sensing a smell associated with a chemical species. The processing circuit further includes an artificial intelligence engine to enhance smell recognition capabilities of the device.

20 Claims, 6 Drawing Sheets

SYSTEMS AND METHODS FOR ENVIRONMENT SENSING

CROSS-REFERENCE TO RELATED APPLICATIONS

This application is a continuation of the provisional Application No. 62/566,295, filed Sep. 29, 2017, which is incorporated by reference herein by its entirety.

TECHNICAL FIELD

The present description relates generally to sensor technology, and more particularly, to systems and methods for environment sensing.

BACKGROUND

Many mobile electronic devices are equipped with sensors and transducers that enable the device to perform far more functionalities than communications. Media playing, photography, location detection, online shopping, social media, online banking, calendar, health applications such as heart beat, blood pressure and blood oxygen level measurement are among the numerous applications that a smart mobile communication device can facilitate. Further, smart portable communication devices (e.g., smart phone and smart watches) can interact with the user through some of human senses such as vision, hearing, and touch.

There are electronic devices that can detect an analyte in fluids (e.g., liquids, gases and vapors) with the help of pattern-recognition. However, there are no portable communication devices that can mimic users' senses for smell and taste. The ability to smell various flavors when combined, for example, with photo recognition can open a new horizon to smart device applications. The new applications may be in a number of areas including health, safety, security, networking and other areas. For example, in the health and safety areas, a smell-enabled (e.g., e-nose) smart communication device may be able to alert users about dangerous levels of gases such as carbon monoxide, natural gas and other toxic and/or hazardous gases, or measure compounds in human sweat and alert the user about his sugar levels, for example.

BRIEF DESCRIPTION OF THE DRAWINGS

Certain features of the subject technology are set forth in the appended claims. However, for purposes of explanation, several embodiments of the subject technology are set forth in the following figures.

DETAILED DESCRIPTION

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, the subject technology is not limited to the specific details set forth herein and may be practiced without one or more of the specific details. In some instances, structures and components are shown in block diagram form in order to avoid obscuring the concepts of the subject technology.

In one or more aspects, the subject technology is directed to systems and methods for environmental sensing including identifying smells associated with gaseous species released from various substances. The subject technology can be implemented as a stand-alone device or can be integrated with a portable communication device such as a smart phone or a smart watch. Integration of environmental sensors with consumer electronic platforms is valuable as it could enable new features such as environmental and health monitoring and other various features.

In some implementations, a portable communication device of the subject technology may include one or more sensors, a number of electrodes and a processing circuit. The processing circuit can apply a bias supply voltage (e.g., a DC voltage) and an AC voltage (e.g., a time-varying voltage having a periodic waveform such as a sinusoidal or a square waveform) to the pair of electrodes and can process output signals from the sensors. The sensors can be ionic liquid sensors tuned for sensing a smell associated with one or more chemical species. The processing circuit may further rely on artificial intelligence (AI), for example, use an artificial intelligence (AI) engine to enhance smell recognition capabilities of the device. In some implementations, the ionic liquid sensors are contained in enclosures formed by micro electro-mechanical system (MEMS) structural elements and a surface of a semiconductor chip that includes the processing circuit.

Figure 1:
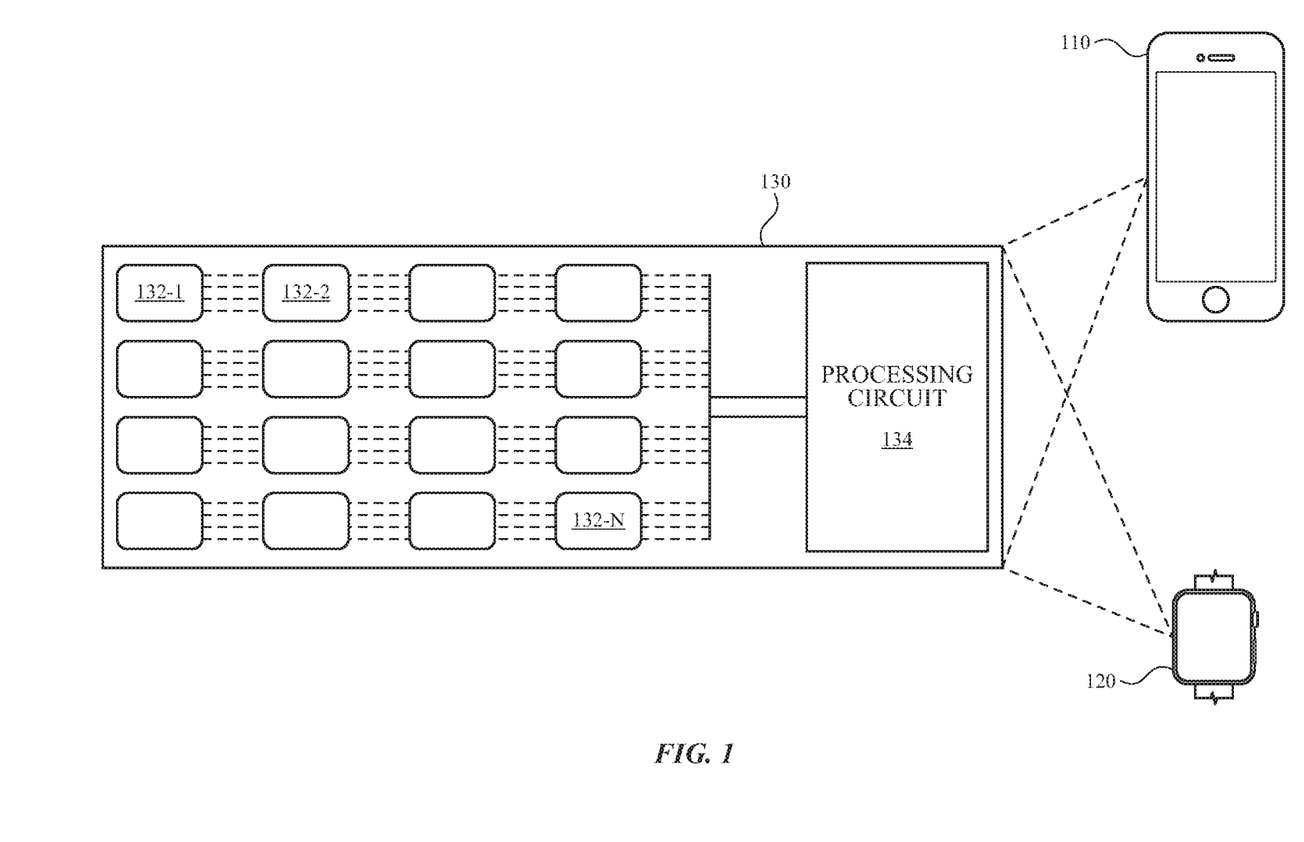
FIG. 1 is a high-level diagram illustrating examples of portable communication devices with environmental sensing capability, in accordance with one or more aspects of the subject technology.

FIG. 1 is a high-level diagram illustrating examples of portable communication devices 110 and 120 with environmental sensing capability, in accordance with one or more aspects of the subject technology. The environmental sensing capability of the subject technology can be integrated with a portable communication device such as a smart phone 110 or a smart watch 120 to enable the smart phone 110 or the smart watch 120 to sense environmental gases, for example, to recognize odors (smells) associated with various substances. The integration can make the portable communication device a platform with the capability of running an entire new dimension of applications, for instance, in health, safety, security, networking and other areas.

The portable communication device of the subject technology (e.g., the smart phone 110 or the smart watch 120) includes an environmental sensing chip 130 that can communicate with other components of the portable communication device such as a central processor and memory (e.g., no-volatile or volatile memory) of the portable communication device. The environmental sensing chip 130 (hereinafter "chip 130") may include a number of environmental sensors 132 (e.g., patches 132-1, 132-2 . . . 132-N) and a processing circuit 134. The chip 130 can be a semiconductor chip such as a silicon chip or a chip made of other semiconductor materials.

The environmental sensors 132 can be gas sensors that can detect many environmental gases including gases associated with chemical compound or species that have aroma, odor or flavor. Each environmental sensor 132 is connected to a pair of electrodes. In some implementations, the environmental sensors 132 are made of an ionic liquid material. For example, each sensor is made of a different ionic liquid material with a different absorption coefficient for various flavors/odors. The absorption coefficient is associated with certain basic electrochemical properties of the ionic liquid material including parameters such as an electrode potential, a DC resistance, an AC impedance or other parameters. The electrodes are continuously monitored and the measured parameters are reported to a central processing unit (CPU) of the portable communication device.

In some implementations, the processing circuit 134 integrated on the chip 130 and interfaced with the environmental sensors 132, can provide biasing for and process the output signal from the environmental sensors 132, as described in more details herein. In one or more implementations, the chip 130 may include about 100-200 environmental sensors 132 (e.g. patches) and may occupy an area of about 5 mm×5 mm or smaller.

Figure 2:
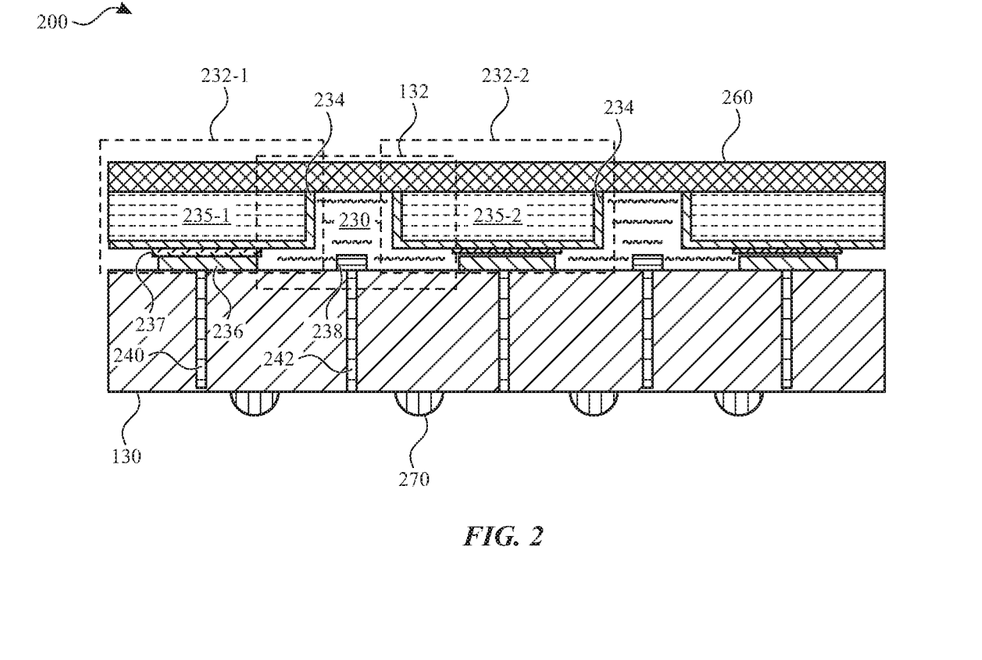
FIG. 2 is a schematic diagram illustrating a cross-sectional view of examples of environmental sensing devices integrated with a semiconductor chip, in accordance with one or more aspects of the subject technology.

FIG. 2 is a schematic diagram illustrating a cross-sectional view 200 of examples of environmental sensing devices 132 integrated with a semiconductor chip 130, in accordance with one or more aspects of the subject technology. Each environmental sensing devices 132 (herein after "sensor 132") includes a sensing material 230 enclosed in an enclosure formed by MEMS structural elements 232 (e.g., 232-1 and 232-2) and a surface (e.g., top surface in FIG. 2) of the semiconductor chip 130 (hereinafter "chip 130").

The sensing material 230 can be an ionic liquid material having variable electrical properties (e.g., DC resistance and/or AC impedance) that can change as a result of dissolving different gases. In some implementations, the ionic liquid can be molten salts with large organic cation and anions or salts that are liquid in room temperature. These materials are environmental friendly and non-flammable and have near zero vapor pressure and suitable thermal and chemical stability.

Walls of the enclosure of the sensor 132 are formed by the MEMS structural elements 232. The MEMS structural elements 232 include bulk materials (e.g., silicon or other suitable material) 235 (e.g., 235-1 and 235-2) coated with an outer layer 234 that is in contact with a first electrode 236 (e.g., anode) of the sensor 132. The outer layer 234 is coupled to the first electrode 236, via a conductive bond material 237. The first electrode 236 is coupled to a first through-silicon via (TSV) 240 of the chip 130. The enclosure of the sensor 132 further includes an air permeable layer 260 (e.g., a frit glass layer) that covers the MEMS structural elements. The air permeable layer 260 allows air including gaseous species to enter the sensor 132, while preventing environmental aggressors such as liquids (e.g., water, moister, and oil) and dust to affect the sensing material 230. The enclosure further includes a second electrode 238 (e.g., cathode) in contact with the sensing material 230 (e.g., ionic liquid) and coupled to a second TSV 242 of the chip 130. The first electrode 236, the second electrode 238, and the outer layer 234 can be made of electrically conductive materials including metals such as silver, aluminum, copper, tungsten or other conductive materials.

Among advantageous features of the sensors 132 is compatibility with electronic integrated circuit (IC) manufacturing processes. For example, MEMS structural elements 232 can be fabricated by the steps of 1) etching to create openings with diameters of about 100-200 µm (e.g., using a deep reactive ion etch process) in a bulk silicon layer (e.g., about 200-300 µm thick) to separate portions forming the bulk material 235; 2) coating (e.g., by conformal metal coating) the outer layer 234; 3) flipping (e.g., using flip chip process) the formed structure; and 4) bonding the formed structure to the first electrodes 236 of the chip 130. The chip 130 further includes conductive bumps 270 for bonding to other chips of the potable communication device (e.g., 110 or 120 of FIG. 1).

Figure 3:
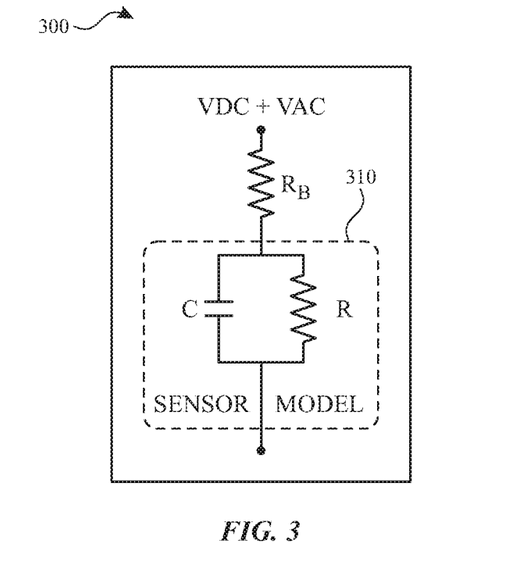
FIG. 3 is a schematic diagram illustrating an example circuit model of an environmental sensing device, in accordance with one or more aspects of the subject technology.

FIG. 3 is a schematic diagram illustrating an example circuit model 300 of an environmental sensing device, in accordance with one or more aspects of the subject technology. The circuit model 300 may for example represent electrical characteristics of the sensors 132 of FIGS. 1 and 2. As discussed above, the sensing material 230 of the sensor 132 can be an ionic liquid material with parameters such as a DC resistance R and an AC impedance that can be represented by the capacitance C or a parallel combination of the resistance R and the capacitance C. The sensor 132, as represented by the RC circuit 310, can be coupled to a DC voltage (VDC) and an AC voltage (VAC) through a bias resistance RB.

Figure 4:
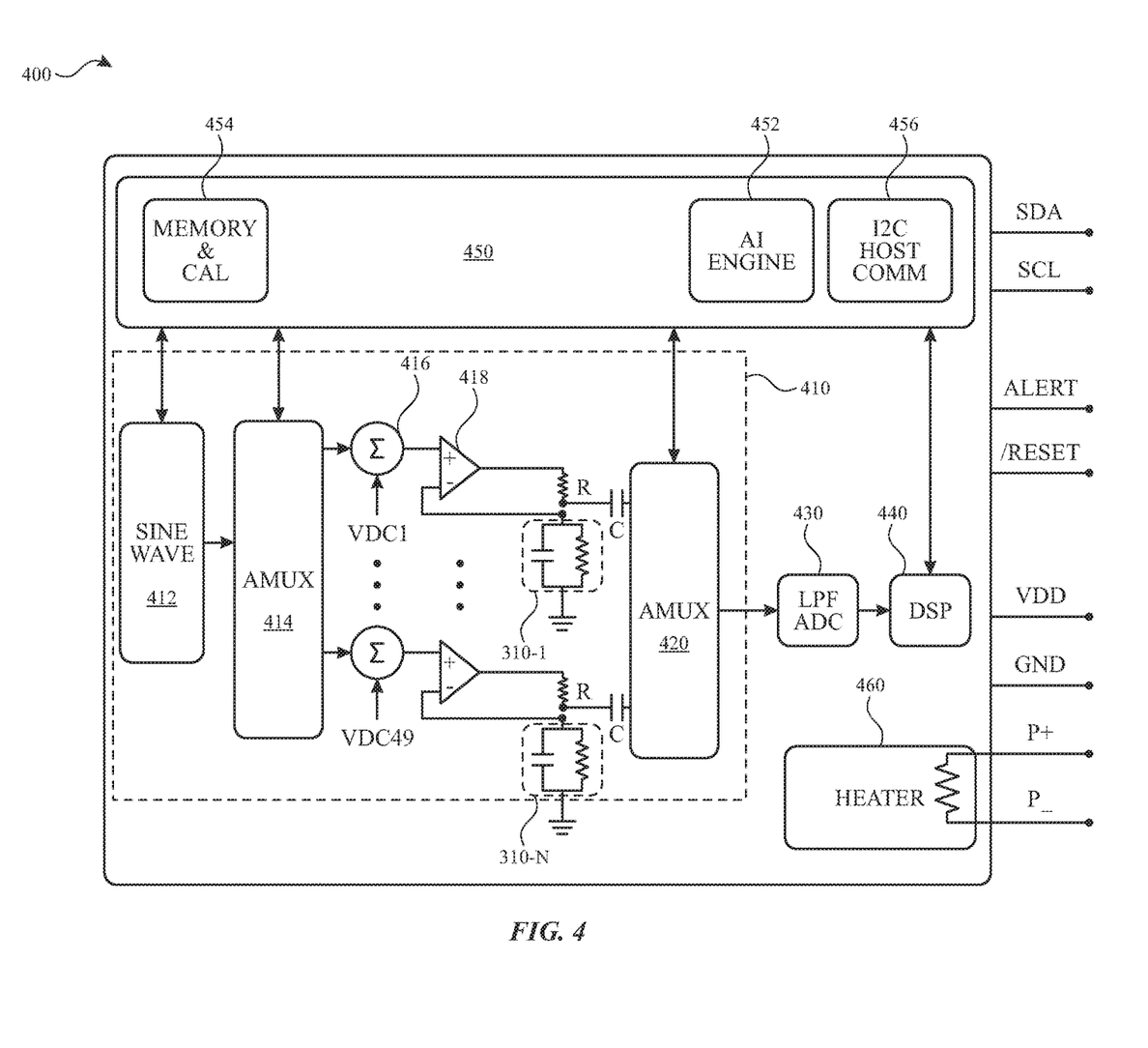
FIG. 4 is a block diagram illustrating an example processing circuit for an environmental sensing device, in accordance with one or more aspects of the subject technology.

FIG. 4 is a block diagram illustrating an example processing circuit 400 for an environmental sensing device, in accordance with one or more aspects of the subject technology. The processing circuit 400 is an example implementation of the processing circuit 134 of FIG. 1 and includes an analog processing circuit 410, a digital processing circuit 450, a low-pass filter (LPF) and analog-to-digital converter (ADC) circuit 430, a digital signal processing (DSP) circuit 440 and a heater 460. The analog processing circuit 410 provides AC and DC bias voltages for the sensors 132 of FIG. 1 (represented by the RC circuits 310) and preprocesses the output signals from the sensors.

The analog processing circuit 410 includes a signal generator 412, a first analog multiplexer (AMUX) 414, summer circuits 416, operational amplifiers (Op Amps) 418, resistors R, capacitors C, and a second AMUX 420. The signal generator 412 can generate a periodic voltage (e.g., with a sinusoidal or square waveform) with a frequency within a range of a few Hz to hundreds of KHz. The first AMUX 414 can generate multiple AC voltages to be used for multiple sensors (e.g., represented by RC circuits 310-1 . . . 310-N). Each AC voltage can be combined with a pre-defined DC bias voltage (e.g., within a range of about 0.5V to 5V) using a summer circuit 416. The pre-defined DC bias voltages for different sensors can be different as the sensors are tuned, for example, for different flavors or odors. The Op Amps 418 apply the combined AC and DC voltages to the RC circuits 310 (representing sensors). The output signal derived from each RC circuit 310 is a measure of the DC resistance and AC impedance changes of the RC circuit 310 (representing the ionic liquid sensors) as a result of dissolving a specific gas. The second AMUX 420 multiplexes the output signals (the DC voltage components are blocked by capacitors C) from the RC circuits 310 into an analog signal that is fed to the LPF and ADC circuit 430 for filtering and conversion to a digital data. The digital data is processed by the DSP 440 that can scale and organize the digital data for processing by the digital processing circuit 450.

The digital processing circuit 450 includes, but is not limited to, an AI engine 452, memory and calibration module 454 and a known communication interface 456 (e.g., an inter-integrated circuit (I2C) host communication interface). The AI engine 452 can analyze the digital data from the DSP 440 and can be trained to enhance smell (flavor) recognition of the device that hosts the sensors. The AI engine 452 can be stochastically trained prior to the implementation in the host device. The identification of flavors may be greatly enhanced by combining the results of the analysis by the AI engine 452 with visual identification (e.g., by a camera of the host device) of the object (e.g., a flower), the odor of which is sensed. The AI engine 452 has the opportunity of being adaptive and trainable in the field with new experiences.

Another aspect of using the ionic liquid sensors is to prevent sensor saturation by reversing the dissolution process, for example, by applying a suitable voltage or an appropriate temperature to the sensor. The appropriate temperature (e.g., within a range of about 100° C. to 200° C.) can be applied to the sensor by the heater 460 which is controlled by P+ and P− ports of the processing circuit 400. The processing circuit 400 includes other known ports labeled as ground (GND), VDD, /RESET, ALERT, serial clock line (SCL) and serial data line (SDA).

Figure 5:
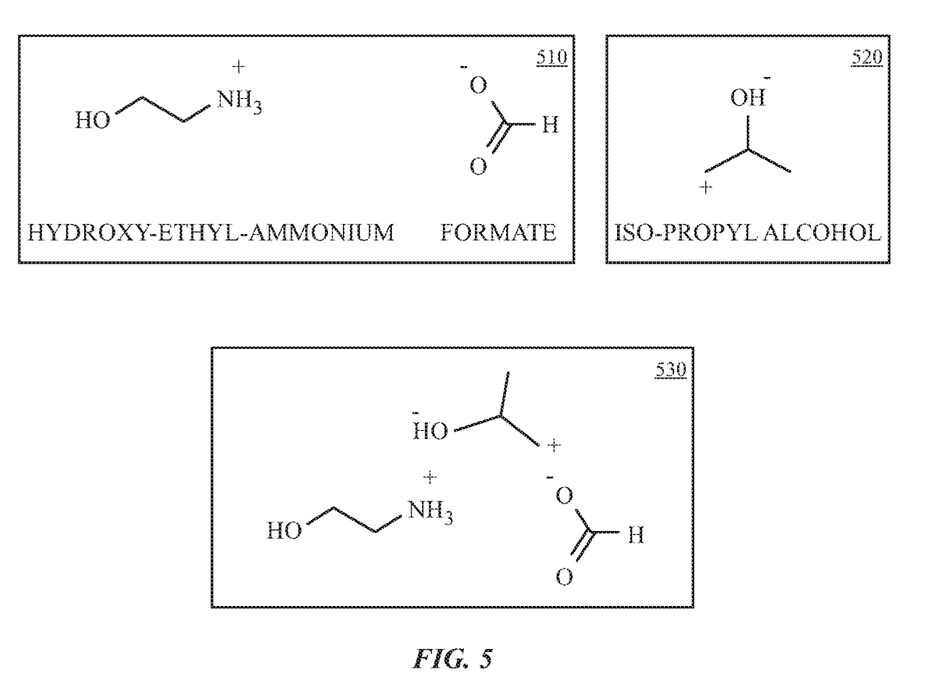
FIG. 5 is a diagram illustrating an example mechanism for dissolving of gases by an ionic liquid environmental sensing material, in accordance with one or more aspects of the subject technology.

FIG. 5 is a diagram illustrating an example mechanism for dissolving of gases by an ionic liquid environmental sensing material, in accordance with one or more aspects of the subject technology. The dissolving mechanism of ionic liquids is different from that of ordinary solvents such as water, which is a semi-polar molecule with a dipole moment and can dissolve most polar materials by bonding separately to ions of the polar material. An ionic liquid 510, for example, formed of hydroxy-ethyl-ammonium and formate (e.g., an anion derived from formic acid) ionic molecules, can selectively dissolve a compound 520 (e.g., iso-propyl alcohol), the smell of which is to be sensed. The selective dissolution as represented by the resultant molecule 530 is based on matching three dimensional (3-D) geometry and dipole moments of the ionic liquid 510 and the dissolved compound 520.

Figure 6:
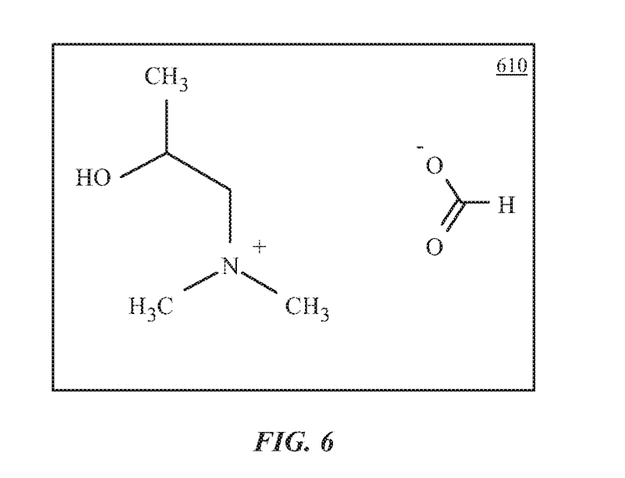
FIG. 6 is a diagram illustrating an example of an ionic liquid environmental sensing material tuned for dissolving of a particular gas, in accordance with one or more aspects of the subject technology.

FIG. 6 is a diagram illustrating an example of an ionic liquid environmental sensing material tuned for dissolving of a particular gas, in accordance with one or more aspects of the subject technology. The ionic liquid 510 of FIG. 5 (e.g., hydroxy-ethyl-ammonium plus formate) can be tuned to selectively dissolve another compound such as ethanol to form the resultant molecular structure 610. In some aspects, the tuning of an ionic liquid can be performed prior to its use as a sensing material. Examples of cation ionic liquids are imidazolium, thiazolium and pyrazolium that can form a myriad of combinations, each with a bit different physical property. For example, gas absorption can be programmed into the molecular structure of the ionic liquid as a physical property. The shape and dipole moment of the molecule has to be such that it preferentially accepts the gas molecule of interest.

Figure 7:
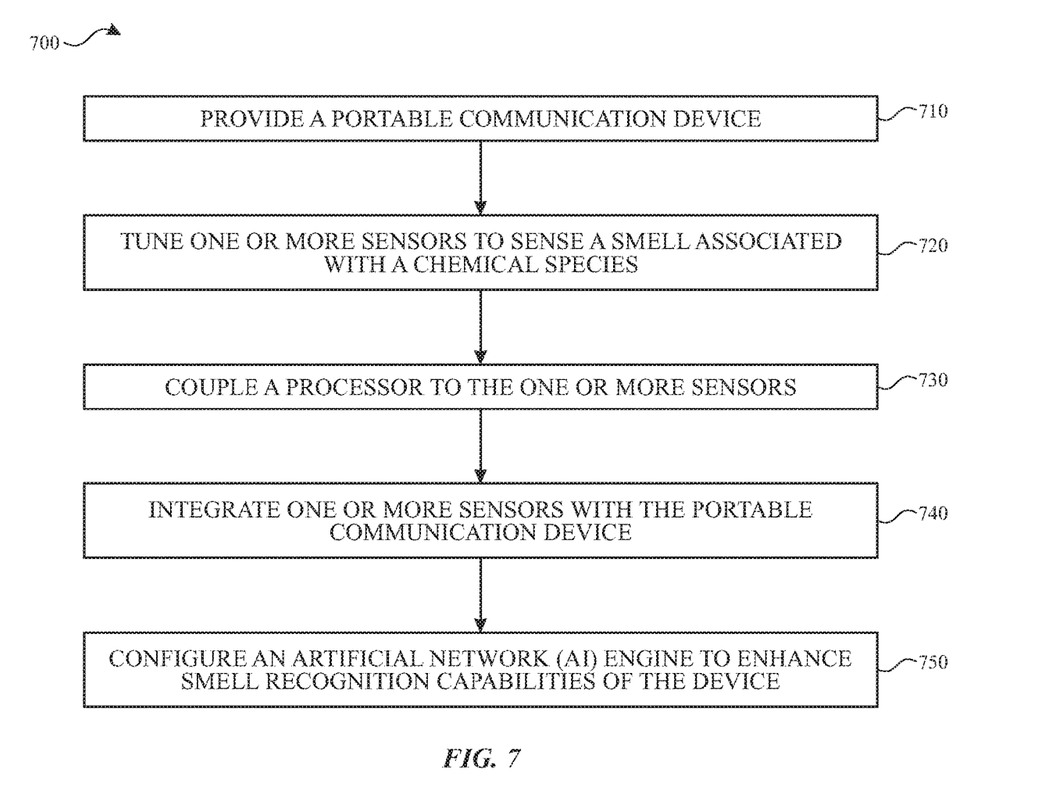
FIG. 7 is a flow diagram illustrating a method of providing a portable communication device with environmental sensing capability, in accordance with one or more aspects of the subject technology.

FIG. 7 is a flow diagram illustrating a method 700 of providing a portable communication device with environmental sensing capability, in accordance with one or more aspects of the subject technology. The method 700 begins with providing a portable communication device (e.g., 110 or 120 of FIG. 1) (710). One or more sensors (e.g., 132 of FIG. 1) are tuned to sense a smell associated with a chemical species (720). A processor circuit (e.g., 134 of FIG. 1 or 400 of FIG. 4) including an AI engine (e.g., 452 of FIG. 4) is coupled to the sensors (730). The sensors are integrated with the portable communication device (see FIG. 1) (740). The AI engine is configured to enhance smell recognition capabilities of the portable communication device (750).

Figure 8:
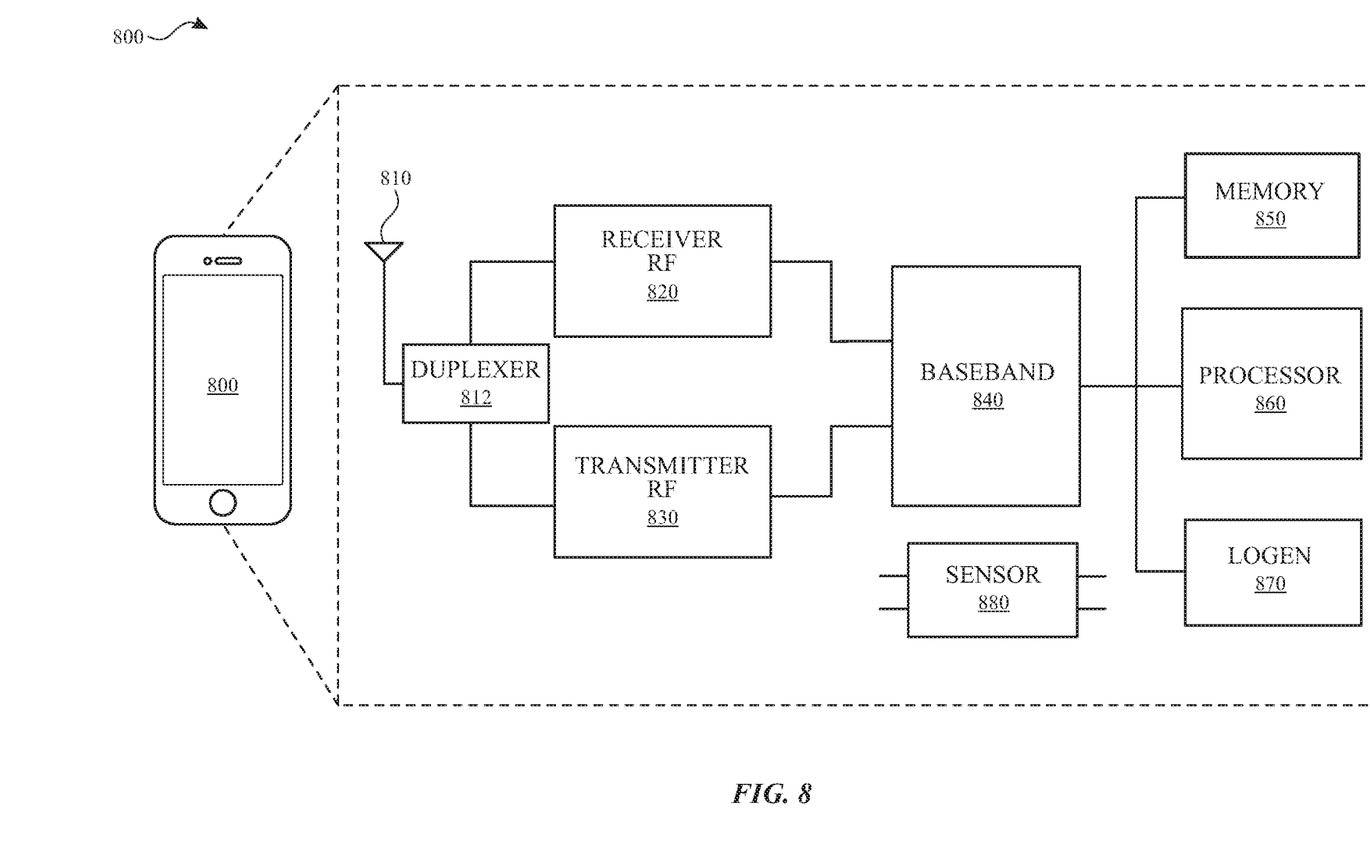
FIG. 8 is a block diagram illustrating an example wireless communication device, within which one or more environmental sensors of the subject technology can be integrated.

FIG. 8 is a block diagram illustrating an example wireless communication device, within which one or more environmental sensors of the subject technology can be integrated. The wireless communication device 800 may comprise a radio-frequency (RF) antenna 810, a receiver 820, a transmitter 830, a baseband processing module 840, a memory 850, a processor 860, a local oscillator generator (LOGEN) 870 and one or more sensors 880. In various embodiments of the subject technology, one or more of the blocks represented in FIG. 8 may be integrated on one or more semiconductor substrates. For example, the blocks 820-870 may be realized in a single semiconductor chip or a single system on a semiconductor chip, or may be realized in a multi-semiconductor chip semiconductor chipset.

The receiver 820 may comprise suitable logic circuitry and/or code that may be operable to receive and process signals from the RF antenna 810. The receiver 820 may, for example, be operable to amplify and/or down-convert received wireless signals. In various embodiments of the subject technology, the receiver 820 may be operable to cancel noise in received signals and may be linear over a wide range of frequencies. In this manner, the receiver 820 may be suitable for receiving signals in accordance with a variety of wireless standards, Wi-Fi, WiMAX, Bluetooth, and various cellular standards. In various embodiments of the subject technology, the receiver 820 may not require any SAW filters and few or no off-semiconductor chip discrete components such as large capacitors and inductors.

The transmitter 830 may comprise suitable logic circuitry and/or code that may be operable to process and transmit signals from the RF antenna 810. The transmitter 830 may, for example, be operable to up-convert baseband signals to RF signals and amplify RF signals. In various embodiments of the subject technology, the transmitter 830 may be operable to up-convert and amplify baseband signals processed in accordance with a variety of wireless standards. Examples of such standards may include Wi-Fi, WiMAX, Bluetooth, and various cellular standards. In various embodiments of the subject technology, the transmitter 830 may be operable to provide signals for further amplification by one or more power amplifiers.

The duplexer 812 may provide isolation in the transmit band to avoid saturation of the receiver 820 or damaging parts of the receiver 820, and to relax one or more design requirements of the receiver 820. Furthermore, the duplexer 812 may attenuate the noise in the receive band. The duplexer may be operable in multiple frequency bands of various wireless standards.

The baseband processing module 840 may comprise suitable logic, circuitry, interfaces, and/or code that may be operable to perform processing of baseband signals. The baseband processing module 840 may, for example, analyze received signals and generate control and/or feedback signals for configuring various components of the wireless communication device 800, such as the receiver 820. The baseband processing module 840 may be operable to encode, decode, transcode, modulate, demodulate, encrypt, decrypt, scramble, descramble, and/or otherwise process data in accordance with one or more wireless standards.

The processor 860 may comprise suitable logic, circuitry, and/or code that may enable processing data and/or controlling operations of the wireless communication device 800. In this regard, the processor 860 may be enabled to provide control signals to various other portions of the wireless communication device 800. The processor 860 may also control transfers of data between various portions of the wireless communication device 800. Additionally, the processor 860 may enable implementation of an operating system or otherwise execute code to manage operations of the wireless communication device 800. In some aspects, the processor 860 may partially or entirely perform functionalities of the DSP 440 and the AI engine 452 of FIG. 4.

The memory 850 may comprise suitable logic, circuitry, and/or code that may enable storage of various types of information such as received data, generated data, code, and/or configuration information. The memory 850 may comprise, for example, RAM, ROM, flash, and/or magnetic storage. In various embodiment of the subject technology, information stored in the memory 850 may be utilized for configuring the receiver 820 and/or the baseband processing module 840. In some embodiments, the memory 850 may perform the functionalities of the memory and calibration module 454 of FIG. 4.

The local oscillator generator (LOGEN) 870 may comprise suitable logic, circuitry, interfaces, and/or code that may be operable to generate one or more oscillating signals of one or more frequencies. The LOGEN 870 may be operable to generate digital and/or analog signals. In this manner, the LOGEN 870 may be operable to generate one or more clock signals and/or sinusoidal signals. Characteristics of the oscillating signals such as the frequency and duty cycle may be determined based on one or more control signals from, for example, the processor 860 and/or the baseband processing module 840.

In operation, the processor 860 may configure the various components of the wireless communication device 800 based on a wireless standard according to which it is desired to receive signals. Wireless signals may be received via the RF antenna 810 and amplified and down-converted by the receiver 820. The baseband processing module 840 may perform noise estimation and/or noise cancellation, decoding, and/or demodulation of the baseband signals. In this manner, information in the received signal may be recovered and utilized appropriately. For example, the information may be audio and/or video to be presented to a user of the wireless communication device, data to be stored to the memory 850, and/or information affecting and/or enabling operation of the wireless communication device 800. The baseband processing module 840 may modulate, encode, and perform other processing on audio, video, and/or control signals to be transmitted by the transmitter 830 in accordance with various wireless standards.

The one or more sensors 880 may include the sensors 132 of FIG. 1. The sensor 132 of the subject technology can be readily integrated into the wireless communication device 800, in particular when the wireless communication device 800 is a smart mobile phone or a smart watch.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but are to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the subject disclosure.

The predicate words "configured to", "operable to", and "programmed to" do not imply any particular tangible or intangible modification of a subject, but, rather, are intended to be used interchangeably. For example, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as a "configuration" does not imply that such configuration is essential to the subject technology or that such configuration applies to all configurations of the subject technology. A disclosure relating to a configuration may apply to all configurations, or one or more configurations. A phrase such as a configuration may refer to one or more configurations and vice versa.

The word "example" is used herein to mean "serving as an example or illustration." Any aspect or design described herein as "example" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A portable communication device, the device comprising:
   one or more sensors;
   a pair of electrodes associated with each sensor of the one or more sensors; and a processing circuit configured to apply a bias supply voltage to the pair of electrodes and to process output signals from the one or more sensors, wherein:

each sensor of the one or more sensors comprises an ionic liquid sensor tuned for sensing a smell associated with a chemical species, and the processing circuit further comprises an artificial intelligence engine configured to enhance smell recognition capabilities of the device.

2. The device of claim 1, wherein each ionic liquid sensor is contained in an enclosure formed by micro electro-mechanical system (MEMS) structural elements and a surface of a semiconductor chip including the processing circuit.

3. The device of claim 2, wherein the enclosure further includes an air permeable layer that covers the MEMS structural elements.

4. The device of claim 2, wherein the enclosure further includes a second electrode coupled to a second TSV of the semiconductor chip.

5. The device of claim 2, wherein the semiconductor chip further includes a heater configured to raise temperatures of ionic liquid sensors to facilitate reversal of boding of the chemical species to the ionic liquid sensors.

6. The device of claim 2, wherein the MEMS structural elements form walls of the enclosure, and wherein each of the MEMS structural elements includes an outer layer formed by an electrically conductive material.

7. The device of claim 6, wherein the electrically conductive material comprises a first electrode of the sensor and is coupled to a first through-silicon via (TSV) of the semiconductor chip.

8. The device of claim 1, wherein each of the one or more sensors includes an inherent variable resistance and an inherent variable capacitance, wherein values of the inherent variable resistance and the inherent variable capacitance depend on the smell associated with the chemical species.

9. The device of claim 1, wherein the processing circuit further comprises an analog multiplexer, a low pass filter and an analog-to-digital converter (ADC) and a digital signal processing circuit to preprocess the output signals from the one or more sensors for analysis by the artificial intelligence engine.

10. The device of claim 9, wherein preprocessing comprises scaling and organizing a digitized signal produced by the ADC.

11. The device of claim 1, wherein the artificial intelligence engine is configured to enhance smell recognition capabilities of the device based on smell information stored in a memory.

12. A portable communication device, the device comprising:

one or more sensors integrated with a semiconductor chip and configured to sense one or more gases and generate sensor signals; and a processing circuit configured to apply a DC supply voltage and an AC voltage to a pair of electrodes of each sensor of the one or more sensors and to process the sensor signals, wherein:

each sensor of the one or more sensors is tuned for sensing a smell associated with a gas of the one or more gases, and the processing circuit further comprises an artificial intelligence engine configured to enhance smell recognition capabilities of the device based on smell information stored in memory.

13. The device of claim 12, wherein each sensor of the one or more sensors comprises an ionic liquid sensor contained in an enclosure formed by micro electro-mechanical system (MEMS) structural elements and a surface of the semiconductor chip, wherein each MEMS structural element includes a conductive layer forming a first electrode of the sensor that is coupled to a first through-silicon via (TSV) of the semiconductor chip.

14. The device of claim 13, wherein the enclosure further includes an air permeable layer configured to cover the MEMS structural elements, and a second electrode coupled to a second TSV of the semiconductor chip.

15. The device of claim 12, wherein each of the one or more sensors includes an intrinsic resistance and an intrinsic capacitance, wherein the sensor signals are generated based on variation of the intrinsic resistance and the intrinsic capacitance.

16. The device of claim 12, wherein the processing circuit further comprises an analog multiplexer, a low pass filter and an analog-to-digital converter (ADC) to preprocess the sensor signals and to generate digital signals.

17. The device of claim 16, wherein the processing circuit further comprises a digital signal processing (DSP) circuit configured to scale and organize the digital signals for analysis by the artificial intelligence engine.

18. A system comprising:

one or more transceivers;
one or more processors;
memory coupled to the one or more processors; and
a sniffer unit comprising:
  one or more ionic liquid sensors tuned for sensing a smell associated with a chemical substance;
  an analog processing circuit configured to apply a bias supply voltage and a periodic voltage to each sensor of the one or more ionic liquid sensors; and
  an artificial intelligence engine coupled to the memory,
wherein:
the analog processing circuit is further configured to process output signals from the one or more ionic liquid sensors, and
the artificial intelligence engine is configured to enhance smell recognition capabilities of the sniffer unit.

19. The system of claim 18, wherein the artificial intelligence engine is configured to enhance smell recognition capabilities of the sniffer unit by using smell information stored in the memory.

20. The system of claim 19, wherein the smell information stored in the memory are associated with a number of applications including at least one of aviation safety, hazardous gas detection, spoiled food material detection, body odor detection and health applications.

* * * * *